United States Patent [19]

Baichwal et al.

[11] Patent Number: 5,399,358
[45] Date of Patent: Mar. 21, 1995

[54] SUSTAINED RELEASE FORMULATIONS FOR 24 HOUR RELEASE OF METROPROLOL

[75] Inventors: Anand R. Baichwal, Wappingers Falls, N.Y.; John N. Staniforth, Bath, England

[73] Assignee: Edward Mendell Co., Inc., Patterson, N.Y.

[21] Appl. No.: 151,272

[22] Filed: Nov. 12, 1993

[51] Int. Cl.⁶ ............................................... A61K 9/22
[52] U.S. Cl. ...................... 424/464; 424/468; 424/469; 424/484; 424/485; 424/488
[58] Field of Search ............... 424/464, 468, 469, 484, 424/485, 488; 514/651

[56] References Cited

U.S. PATENT DOCUMENTS

| | | | |
|---|---|---|---|
| 4,303,691 | 12/1981 | Sand et al. | 426/573 |
| 4,792,452 | 12/1988 | Howard et al. | 424/475 |
| 4,795,642 | 7/1989 | Cohen et al. | 424/455 |
| 4,857,331 | 8/1989 | Shaw et al. | 424/484 |
| 4,871,549 | 10/1989 | Ueda et al. | 424/494 |
| 4,886,669 | 12/1989 | Ventouras | 424/469 |
| 4,942,040 | 7/1990 | Ragnarsson et al. | 424/486 |
| 4,957,745 | 9/1990 | Jonsson et al. | 424/461 |
| 4,968,508 | 11/1990 | Oren et al. | 424/468 |
| 4,994,276 | 2/1991 | Baichwal et al. | 424/440 |
| 5,032,406 | 7/1991 | Dansereau et al. | 424/464 |
| 5,047,244 | 9/1991 | Sandvordecker et al. | 424/435 |
| 5,081,154 | 1/1992 | Appelgren et al. | 514/651 |
| 5,128,143 | 7/1992 | Baichwal et al. | 424/464 |
| 5,135,757 | 8/1992 | Baichwal et al. | 424/465 |
| 5,169,638 | 12/1992 | Dennis et al. | 424/457 |
| 5,169,639 | 12/1992 | Baichwal et al. | 424/468 |
| 5,271,943 | 12/1993 | Bogart et al. | 424/484 |
| 5,330,761 | 7/1994 | Baichwal et al. | 424/469 |
| 5,330,763 | 7/1994 | Gole et al. | 424/484 |

*Primary Examiner*—Thurman K. Page
*Assistant Examiner*—Amy Hulina
*Attorney, Agent, or Firm*—Steinberg, Raskin & Davidson

[57] ABSTRACT

A sustained release oral solid dosage form of metoprolol pharmaceutical formulation includes a sustained release excipient including a gelling agent, an inert pharmaceutical diluent, a cationic cross-linking agent, and metoprolol provides release of metoprolol for at least about 24 hours. In certain embodiments, the sustained release formulation further includes a hydrophobic material.

34 Claims, No Drawings

SUSTAINED RELEASE FORMULATIONS FOR 24 HOUR RELEASE OF METROPROLOL

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods.

For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements.

While many controlled and sustained-release formulations are already known, it is often not possible to readily predict whether a particular sustained-release formulation will provide the desired sustained release for a particular drug, and it has generally been found that it is necessary to carry out considerable experimentation to obtain sustained release formulations of such drugs having the desired rate of release when ingested.

There have been a number of patents in the prior art which relate to controlled release metoprolol formulations. For example, U.S. Pat. No. 5,169,638 describes a buoyant controlled release pharmaceutical formulation in the form of a powder filled capsule in which an active ingredient of a basic character exhibits a pH-independent controlled release. The powder comprises the active agent, which may be metoprolol, a water-soluble salt of polyuronic acid, a pH-independent hydrocolloid gelling agent (e.g., hydroxypropylmethylcellulose, methylcellulose or hydroxypropylcellulose), and a binder (HPMC). The formulation is free of calcium ion and carbon dioxide producing material and is said to float gastric juices so that it will have extended residence time in the stomach.

U.S. Pat. No. 4,792,452 describes controlled release pharmaceutical compositions which are said to provide pH-independent release for a basic drug such as metoprolol. The formulations include a pH-dependent polymer which is a salt of alginic acid, a pH-independent hydrocolloid gelling agent and a binder. The salt of the alginic acid is preferably sodium alginate or potassium alginate. The weight ratio of the alginic acid salt to the hydrocolloid gelling agent is all within the range 0.1:1 to 10:1, and the formulation is free of calcium ion and carbon dioxide-producing material.

U.S. Pat. No. 4,957,745 also describes a controlled release metoprolol. The preparation includes a plurality of beads comprising metoprolol coated with a polymeric membrane comprising ethylcellulose with or without hydroxypropylmethylcellulose.

U.S. Pat. No. 4,871,549 describes a time controlled explosion system comprising metoprolol, a swelling agent such as a low substituted hydroxypropylcellulose, sodium starch glycolate or carboxymethylcellulose sodium, coated with a water-insoluble coating material so that drug release is caused by the explosion of the membrane after a definite time period.

U.S. Pat. No. 5,081,154 is directed to metoprolol succinate in an oral composition coated with an anionic polymer soluble at pH over 5.5 and a water insoluble quaternary ammonium substituted acrylic polymer.

Previously, a heterodisperse polysaccharide excipient system and controlled release oral solid dosage forms were described in our U.S. Pat. Nos. 4,994,276, 5,128,143, and 5,135,757, all of which are hereby incorporated by reference. These systems are commercially available under the tradename TIMERx TM from Edward Mendell Co., Inc., N.Y., which is the assignee of the present invention. These patents are hereby incorporated by reference.

OBJECTS AND SUMMARY OF THE INVENTION

It is an object of the present invention to provide oral solid sustained release formulations which release metoprolol over a time period of at least about 24 hours, when the formulations are exposed to an environment of use (e.g., the gastrointestinal tract).

It is a further object of the present invention to provide methods for preparing sustained release metoprolol formulations which may be administered to patients on a once-a-day basis, or a desired longer time interval.

The above-mentioned objects and others are achieved by virtue of the present invention, which relates in part to a controlled release formulation comprising a therapeutically effective amount of metoprolol, and a sustained release excipient comprising a heteropolysaccharide gum and a homopolysaccharide gum capable of cross-linking said heteropolysaccharide gum when exposed to an environmental fluid; an inert diluent selected from, e.g., a monosaccharide, a disaccharide a polyhydric alcohol, or mixtures thereof; and an effective amount of a pharmaceutically acceptable water-soluble cationic cross-linking agent to provide a sustained release of the medicament for at least about 24 hours, when the dosage form is exposed to an environmental fluid.

In certain preferred embodiments of the invention, the gum is included in an amount from about 30% to about 60%, and more preferably from about 35% to about 50%, by weight of the final product. The drug to gum ratio may be, e.g., from about 1:1 to about 1:5. More preferably, the drug to gum ratio is from about 1:1.5 to about 1:4.

In certain preferred embodiments, the sustained release excipient further comprises a hydrophobic material in an amount effective to slow the hydration of the gums without disrupting the hydrophilic matrix formed by the heterodisperse polysaccharide when the formulation is exposed to fluids in an environment of use.

The formulations of the present invention are prepared as pharmaceutically acceptable oral solid dosage form, such as tablets.

The present invention is also related to a method for providing a sustained release formulation of metoprolol, comprising preparing a sustained release excipient by (1) dry blending a heteropolysaccharide gum and a homopolysaccharide gum capable of cross-linking said heteropolysaccharide gum when exposed to an environmental fluid, together with a pharmaceutically acceptable inert diluent in desired proportions; (2) wet granulating the mixture; (3) drying the resultant granulate; and (4) milling the dried granulate to obtain a sustained release excipient having a desired particle size. Thereafter, the sustained release excipient is (5) wet granulated with metoprolol or a pharmaceutically acceptable salt thereof, and (6) the resultant granulate is dried. Next, any (7) additional inert excipients are added (e.g., a lubricant) and the resultant mixture is then, e.g., (8) compressed into tablets.

In certain preferred embodiments, the mixture of the sustained release excipient and metoprolol are granulated with a solution of a hydrophobic material in an amount sufficient to slow the hydration of the gums without disrupting the same. Thereafter, any additional inert excipients are added (e.g., a lubricant) and the resultant mixture is then, e.g., compressed into tablets.

The present invention is further related to a sustained release oral solid dosage form for absorption of a therapeutically active medicament in the gastrointestinal tract, comprising an effective amount of a metoprolol; and a sustained release excipient comprising a gelling agent comprising a heteropolysaccharide gum and a homopolysaccharide gum capable of cross-linking said heteropolysaccharide gum when exposed to an environmental fluid, and an inert pharmaceutical diluent.

The present invention is further related to a method of treating a patient comprising orally administering the sustained release metoprolol tablets to a patient, thereby providing therapeutically effective blood levels of the medicament for at least about 24 hours.

By "sustained release" it is meant: for purposes of the present invention that the therapeutically active medicament is released from the formulation at a controlled rate such that therapeutically beneficial blood levels (but below toxic levels) of the medicament are maintained over an extended period of time, e.g., providing a 24 hour dosage form.

The term "environmental fluid" is meant for purposes of the present invention to encompass, e.g., an aqueous solution, such as that used for in-vitro dissolution testing, or gastrointestinal fluid.

DETAILED DESCRIPTION

Metoprolol is a beta$_1$-selective (cardioselective) adronoceptor blocking agent. It reduces oxygen demand of the heart, slowing the heart rate and reducing cardiac output at rest and upon exercise; reduces systolic blood pressure, among other things. The drug is available in the United States in as the tartrate salt (Lopressor ®, Geigy Pharmaceuticals), as 50 mg and 100 mg tablets. The effective daily dose is 100 mg to 450 mg, and Lopressor is usually dosed as 100 mg given in two daily doses. Metoprolol is also available as 50 mg, 100 mg and 200 mg extended release tablets in the United States as the succinate salt (Toprol XL ™, Astra Pharmaceutical Products, Inc.), which may be dosed once daily.

As reported in our previously in our U.S. Pat. Nos. 4,994,276, 5,128,143, and 5,135,757, the heterodisperse excipient of the present invention comprising both hetero- and homopolysaccharides which exhibit synergism, e.g., the combination of two or more polysaccharide gums produce a higher viscosity and faster hydration than that which would be expected by either of the gums alone, the resultant gel being faster-forming and more rigid.

In the present invention, it has been found that a sustained release excipient comprising only the heterodisperse polysaccharide, e.g., xanthan gum and locust bean gum, may not sufficient to provide a suitable sustained release of an insoluble medicament to provide a 24 hour formulation, nor to prevent an initial "burst" of drug release from the formulation when the formulation is exposed to a fluid in an environment of use, e.g. an aqueous solution or gastrointestinal fluid.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharides useful in the present invention include galactomannan gums, which are polysaccharides composed solely of mannose and galactose. Preferred galactomannan gums are those which are capable of cross-linking with the heteropolysaccharide. Galactomannans which have higher proportions of unsubstituted mannose regions have been found to achieve more interaction with the heteropolysaccharide when exposed to an environmental fluid. Locust bean gum, which has a higher ratio of mannose to the galactose, is especially preferred as compared to other galactomannans such as guar and hydroxypropyl guar.

The combination of xanthan gum with locust bean gum is an especially preferred gum combination.

It has now been surprisingly discovered that the synergistic combination of heteropolysaccharide/homopolysaccharide gums, when incorporated into an solid oral dosage form containing metoprolol as the active ingredient together with an effective amount of a cationic cross-linking agent to obtain a desirable increased gel strength due to the cross-linking of the heterodisperse polysaccharide, provide a sustained release of metoprolol from the final product which is suitable for once-a-day administration.

In preferred embodiments, the controlled release properties of the final product are optimized when the ratio of heteropolysaccharide gum to galactomannan gum is from about 3:1 to about 1:3, and most preferably about 1:1. However, the sustained release excipient of the invention may comprise from about 1% to about 99% by weight heteropolysaccharide gum and from about 99% to about 1% by weight homopolysaccharide gum.

The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract. Thus, the formulations of the present invention are pH-independent.

The cationic cross-linking agent may be monovalent or multivalent metal cations. The preferred salts are the inorganic salts, including various alkali metal and/or alkaline earth metal sulfates, chlorides, borates, bromides, citrates, acetates, etc. Specific examples of suitable cationic crosslactates, linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride.

In preferred embodiments, the cationic cross-linking agent is included in the sustained release excipient of the present invention in an amount from about 1 to about 20% by weight of the sustained release excipient, and in an amount from about 1% to about 20% by weight of the final dosage form. In preferred embodiments of the present invention, the cationic cross-linking agent comprises about 10% by weight of the sustained release excipient.

The inert filler of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

In certain preferred embodiments of the invention, the sustained release excipient further comprises a hydrophobic material in an amount effective to slow the hydration of the gums without disrupting the hydrophilic matrix formed by the heterodisperse polysaccharide when the formulation is exposed to fluids in an environment of use.

The sustained release excipients of the invention have uniform packing characteristics over a range of different particle size distributions and are capable of processing into tablets using either direct compression, following addition of drug and lubricant powder or conventional wet granulation.

The properties and characteristics of a specific excipient system prepared according to the present invention is dependent in part on the individual characteristics of the homo- and heteropolysaccharide constituents, in terms of polymer solubility, glass transition temperatures etc., as well as on the synergism both between different homo- and heteropolysaccharides and between the homo and heteropolysaccharides and the inert saccharide constituent(s) in modifying dissolution fluid-excipient interactions.

The sustained release excipients of the present invention are preferably prepared via a wet granulation method. However, the pharmaceutical excipients prepared in accordance with the present invention may be prepared according to any agglomeration technique to yield an acceptable excipient product. In wet granulation techniques, the desired amounts of the heteropolysaccharide gum, the homopolysaccharide gum, cationic cross-linking agent and the inert diluent are mixed together and thereafter a moistening agent such as water, propylene glycol, glycerol, alcohol or the like is added to prepare a moistened mass. Next, the moistened mass is dried. The dried mass is then milled with conventional equipment to obtain the desired particle size.

Once the sustained release excipient of the present invention has been prepared, it is then possible to blend the same with metoprolol, e.g., in a V-blender or via wet granulation. An effective amount of any generally accepted pharmaceutical lubricant, including the calcium or magnesium soaps may be added to the above-mentioned ingredients of the excipient at the time the medicament is added, or in any event prior to compression into a solid dosage form. An example of a suitable lubricant is magnesium stearate in an amount of about 0.5% to about 3% by weight of the solid dosage form. An especially preferred lubricant is sodium stearyl fumarate, NF, commercially available under the trade name Pruv ® from the Edward Mendell Co., Inc.

In certain embodiments of the embodiment a hydrophobic material is added to the formulation. This may be accomplished by granulating the sustained release excipient with a solution or dispersion of hydrophobic material prior to the incorporation of the medicament. The hydrophobic material may be selected from ethylcellulose, acrylic and/or methacrylic acid polymers or copolymers, hydrogenated vegetable oils, zein, as well as other pharmaceutically acceptable hydrophobic materials known to those skilled in the art. Other hydrophobic cellulosic materials such as other alkyl celluloses may also be used. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material may be included in the sustained release excipient in an amount from about 1% to about 20% by weight. More preferably, the hydrophobic material may be included in the sustained release excipient in an amount from about 3% to about 12%, and most preferably from about 5% to about 10%, by weight of the final formulation. The hydrophobic material may be dissolved in an organic solvent or dispersed in an aqueous solution for incorporation into the formulation.

The dosage forms of the present invention are preferably tablets. However, the ingredients may also be formulated in a capsule, extruded and spheronized with an active medicament to form pellets, etc.

In certain embodiments, the complete mixture in an amount sufficient to make a uniform batch of tablets is then subjected to tableting in a conventional production scale tableting machine at normal compression pressure, i.e. about 2000–1600 lbs/sq in. However, the mixture should not be compressed to such a degree that there is subsequent difficulty in achieving hydration when exposed to gastric fluid. The average tablet weight may be from about 300 mg to 950 rag. For metoprolol tablets which are to contain about 100 mg of drug, the tablet weight is preferably from about 450 mg to 950 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

The amount of metoprolol or salt thereof incorporated into the unit dose formulations (e.g., tablets) of the present invention may be 50 mg, 100 mg or 200 mg, based on the tartrate salt. Of course, if other metoprolol salts are to be used, the weight of the particular metoprolol salt to be included may be calculated based on an equivalent weight to the tartrate salt.

DETAILED DESCRIPTION OF THE PREFERRED EMBODIMENTS

The following examples illustrate various aspects of the present invention. They are not to be construed to limit the claims in any manner whatsoever.

EXAMPLES 1–3

In Examples 1–3, sustained-release excipients in accordance with the present invention are first prepared, the medicament being added subsequently, and the final mixture then being tableted.

The sustained release excipient is prepared by dry blending the requisite amounts of xanthan gum, locust bean gum, calcium sulfate, and dextrose in a high speed mixer/granulator for 2 minutes. While running choppers/impellers, the water is added to the dry blended mixture, and the mixture is granulated for another 2 minutes. The granulation is then dried in a fluid bed dryer to a loss on drying (LOD) of less than about 10% by weight. In Examples 1–3 the LOD is between 4–7%. The granulation is then milled using 20 mesh screens. The ingredients of the sustained release excipient of Examples 1–3 are set forth in Tables 1 below:

TABLE 1

| PREPARATION OF SUSTAINED RELEASE EXCIPIENT | |
|---|---|
| Component | % |
| Xanthan Gum | 25 |
| Locust Bean Gum | 25 |
| Dextrose | 40 |
| Calcium Sulfate | 10 |
| Water | 10* |

*removed during processing

Next, the sustained release excipient prepared as detailed above is dry blended with the desired amount of metoprolol, provided as the tartrate salt, in a high speed mixer/granulator for 2 minutes. While running choppers/impellers, a solution of ethylcellulose in ethanol is added to the mixture, and the mixture is granulated for another 2 minutes. The granulation is then dried in a fluid bed dryer to an LOD between 4–7%. Net the granulation is milled using 20 mesh screens. A suitable tableting lubricant (Pruv ®, sodium stearyl fumarate, NF, commercially available from the Edward Mendell Co., Inc.) is then added, and the mixture is blended for another 5 minutes. This final mixture is compressed into tablets, each tablet containing 100 mg metoprolol. The tablets of Example 1 weighed 486 mg. The tablets of Example 2 weighed 642 mg. The tablets of Example 3 weighed 753 mg. The drug:gum ratio of the tablets of Example 1 was 1:1.77. The drug:gum ratio of the tablets of Example 2 was 1:2.57. The drug:gum ratio of the tablets of Example 3 was 1:3. The ingredients of the tablets of Examples 1–3 are set forth in Table 2 below:

TABLE 2

| TABLET FORMULATION - EXAMPLES 1–3 | | | | |
|---|---|---|---|---|
| | Component | %-Ex.1 | %-Ex.2 | %-Ex.3 |
| 1. | Sustained Release Excipient | 72.8 | 79.1 | 81.3 |
| 2. | Metoprolol | 20.6 | 15.8 | 13.5 |
| 3. | Ethylcellulose | 5.1 | 5.1 | 5.2 |
| 4. | Pruv ® | 1.5 | 1.5 | 1.5 |
| 5. | Ethanol | 30* | 30* | 30* |

*Removed during processing

Dissolution tests were then carried out on the tablets of Examples 1–3. The dissolution tests are conducted in an automated USP dissolution apparatus (Paddle Type II, pH 6.8 buffer, 100 rpm). The results are set forth in Table 3 below.

TABLE 3

| Dissolution Results - Examples 1–3 | | | |
|---|---|---|---|
| | Percent Released | | |
| Time | Example 1 | Example 2 | Example 3 |
| 0 | 0.0 | 0.0 | 0.0 |
| 2 | 52.7 | 37.7 | 29.7 |
| 4 | 69.7 | 50.9 | 41.9 |
| 8 | 80.9 | 71.1 | 61.5 |
| 12 | 86.7 | 86.4 | 74.8 |
| 16 | 90.6 | 90.3 | 85.1 |
| 20 | 94.4 | 98.1 | 94.1 |
| 24 | 100.0 | 100.0 | 100.0 |

From the results provided in Table 3, it can be seen that as the amount of gum in the formulations is increased, the release rate of the drug (metoprolol) is decreased. It is evident that the tablets of Examples 1–3 provided suitable 24 hour oral solid dosage forms for metoprolol.

EXAMPLES 4–6

In Examples 4–6, sustained release excipients in accordance with the present invention are first prepared, the medicament being added subsequently, and the final mixture then being tableted.

The sustained release excipient is prepared by dry blending the requisite amounts of xanthan gum, locust bean gum, calcium sulfate, and dextrose in a high speed mixer/granulator for 2 minutes. While running choppers/impellers, the water is added to the dry blended mixture, and the mixture is granulated for another 2 minutes. The granulation is then dried in a fluid bed dryer to an LOD of between 4–7%. The granulation is then milled using 20 mesh screens. The ingredients of the sustained release excipient of Examples 4–6 are set forth in Table 4 below:

TABLE 4

| PREPARATION OF SUSTAINED RELEASE EXCIPIENT | |
|---|---|
| Component | % |
| Xanthan Gum | 30 |
| Locust Bean Gum | 30 |
| Dextrose | 30 |

TABLE 4-continued

| PREPARATION OF SUSTAINED RELEASE EXCIPIENT | |
|---|---|
| Component | % |
| Calcium Sulfate | 10 |
| Water | 10* |

*removed during processing

Next, the sustained release excipient prepared as detailed above is dry blended with the desired amount of metoprolol, provided as the tartrate salt, in a high speed mixer/granulator for 2 minutes. While running choppers/impellers, a solution of ethylcellulose in ethanol is added to the mixture, and the mixture is granulated for another 2 minutes. The granulation is then dried in a fluid bed dryer to an LOD between 4–7%. Net the granulation is milled using 20 mesh screens. A suitable tableting lubricant (Pruv ®, sodium stearyl fumarate, NF, commercially available from the Edward Mendell Co., Inc.) is then added, and the mixture is blended for another 5 minutes. This final mixture is compressed into tablets, each tablet containing 100 mg metoprolol. The tablets of Example weighed 552 mg. The tablets of Example 5 weighed mg. The tablets of Example 3 weighed 731 mg. The drug:gum ratio of the tablets of Example 4 was 1:2.5. The drug:gum ratio of the tablets of Example 5 was 1:3.0. The drug:gum ratio of the tablets of Example 6 was 1:3.5. The ingredients of the tablets of Examples 4–6 are set forth in Table 5 below:

TABLE 5

| TABLET FORMULATION - EXAMPLES 4–6 | | | |
|---|---|---|---|
| Component | %-Ex.4 | %-Ex.5 | %-Ex.6 |
| 1. Sustained Release Excipient | 75.4 | 77.9 | 79.8 |
| 2. Metoprolol | 18.6 | 15.6 | 13.7 |
| 3. Ethylcellulose | 5.0 | 5.0 | 5.0 |
| 4. Pruv ® | 1.5 | 1.5 | 1.5 |
| 5. Ethanol | 30* | 30* | 30* |

*Removed during processing

Dissolution tests were then carried out on the tablets of Examples 4–6. The dissolution tests are conducted in an automated USP dissolution apparatus (Paddle Type II, pH 6.8 buffer, 100 rpm). The results are set forth in Table 6 below.

TABLE 6

| Time | Percent Released | | |
|---|---|---|---|
| (hours) | Example 4 | Example 5 | Example 6 |
| 0 | 0.0 | 0.0 | 0.0 |
| 2 | 18.3 | 20.6 | 14.2 |
| 4 | 28.2 | 32.4 | 22.4 |
| 8 | 43.0 | 49.0 | 34.2 |
| 12 | 54.2 | 59.9 | 42.5 |
| 16 | 67.5 | 66.6 | 51.5 |
| 20 | 80.4 | 72.8 | 60.5 |
| 24 | 83.8 | 83.2 | 75.6 |

From the results provided in Table 6, it can be seen once again that as the amount of gum in the formulations is increased, the release rate of the drug (metoprolol) is decreased. The tablets of Examples 4–6 provide an even slower release rate of metoprolol as compared to the formulations of Examples 1–3, and are suitable for a sustained release of metoprolol for 24 hours or longer.

EXAMPLES 7–9

In Examples 7–9, sustained release metoprolol formulations are prepared in accordance with the present invention without the inclusion of the hydrophobic material (e.g., ethylcellulose).

The sustained release excipient is prepared by dry blending the requisite amounts of xanthan gum, locust bean gum, calcium sulfate, and dextrose in a high speed mixer/granulator for 2 minutes. While running choppers/impellers, water is added to the dry blended mixture, and the mixture is granulated for another 2 minutes. The granulation is then dried in a fluid bed dryer to an LOD of between 4–7%. The granulation is then milled using 20 mesh screens. The ingredients of the sustained release excipient of Examples 7–9 are set forth in Table 7 below:

TABLE 7

| PREPARATION OF SUSTAINED RELEASE EXCIPIENT | |
|---|---|
| Component | % |
| Xanthan Gum | 25 |
| Locust Bean Gum | 25 |
| Dextrose | 40 |
| Calcium Sulfate | 10 |
| Water | 10* |

*removed during processing

Next, the sustained-release excipient prepared as detailed above is dry blended with the desired amount of metoprolol, provided as the tartrate salt, in a high speed mixer/granulator for 2 minutes. While running choppers/impellers, water is added to the mixture, and the mixture is granulated for another 2 minutes. The granulation is then dried in a fluid bed dryer to an LOD between 4–7%. Net the granulation is milled using 20 mesh screens. A suitable tableting lubricant (Pruv ®, sodium stearyl fumarate, NF, commercially available from the Edward Mendell Co., Inc.) is then added, and the mixture is blended for another 5 minutes. This final mixture is compressed into tablets, each tablet containing 100 mg metoprolol. The tablets of Example 7 weighed 508 mg. The tablets of Example 8 weighed 711 mg. The tablets of Example 9 weighed 914 mg. The drug:gum ratio of the tablets of Example 7 was 1:2. The drug:gum ratio of the tablets of Example 8 was 1:3. The drug:gum ratio of the tablets of Example 9 was 1:4. The ingredients of the tablets of Examples 7–9 are set forth in Table 8 below:

TABLE 8

| TABLET FORMULATION - EXAMPLES 7–9 | | | |
|---|---|---|---|
| Component | %-Ex.7 | %-Ex.8 | %-Ex.9 |
| 1. Sustained Release Excipient | 78.8 | 84.4 | 87.6 |
| 2. Metoprolol | 19.7 | 14.1 | 10.9 |
| 3. Pruv ® | 1.5 | 1.5 | 1.5 |
| 5. Water | 10* | 10* | 10* |

*Removed during processing

Dissolution tests were then carried out on the tablets of Examples 7–9. The dissolution tests are conducted in an automated USP dissolution apparatus (Paddle Type II, pH 7.5 buffer, 100 rpm). The results are set forth in Table 9 below.

TABLE 9

| Time (hours) | Percent Released | | |
|---|---|---|---|
| | Example 7 | Example 8 | Example 9 |
| 0 | 0.0 | 0.0 | 0.0 |
| 2 | 32.9 | 25.0 | 21.3 |
| 4 | 47.0 | 36.4 | 32.3 |
| 8 | 65.6 | 53.2 | 49.0 |
| 12 | 77.5 | 65.9 | 61.4 |
| 16 | 85.1 | 75.0 | 71.0 |
| 20 | 89.7 | 81.9 | 78.7 |
| 24 | 93.4 | 86.2 | 84.8 |

From the results provided in Table 9, it can be seen once again that as the amount of gum in the formulations is increased, the release rate of the drug (metoprolol) is decreased. The tablets of Examples 7-9 (which did not include ethylcellulose) provide an even slower release rate of metoprolol as compared to the formulations of Examples 1-3 (which included 10% ethylcellulose), and may be suitable for providing a sustained release of metoprolol for 24 hours or longer.

EXAMPLES 10-11

In Examples 10-11, sustained release metoprolol formulations are prepared in accordance with Examples 7-9. The ingredients of the sustained release excipient of Examples 10-11 are identical to those of Examples 7-9. The sustained release excipient is dry blended with the desired amount of metoprolol, provided as the tartrate salt, wet granulated with water, and tabletted as set forth in Examples 7-9. The ingredients and amounts thereof in the tablets of Examples 10-11 are identical with those of Example 7. In Example 10, the tablets were compressed to a tablet size of one-half inch. In Example 11, the tablets were compressed to a tablet size of seven-sixteenths of an inch.

Dissolution tests were then carried out on the tablets of Examples 10-11. The dissolution tests are conducted in an automated USP dissolution apparatus (Paddle Type II, pH 7.5 buffer, 100 rpm). The results are set forth in Table 10 below.

TABLE 10

| Time (hours) | Percent Released | |
|---|---|---|
| | Example 10 Size ½" | Example 11 Size 7/16" |
| 0 | 0.0 | 0.0 |
| 2 | 32.9 | 29.9 |
| 4 | 47.0 | 44.0 |
| 8 | 65.6 | 63.9 |
| 12 | 77.5 | 76.9 |
| 16 | 85.1 | 85.2 |
| 20 | 89.7 | 90.1 |
| 24 | 93.4 | 94.1 |

From the results provided in Table 10, it can be seen that for tablets of the same composition and weight, small changes in diameter and thickness have no significant effect on drug release rate. The tablets of Examples 10-11 would be suitable for providing a sustained release of metoprolol for 24 hours or longer.

The examples provided above are not meant to be exclusive. Many other variations of the present invention would be obvious to those skilled in the art, and are contemplated to be within the scope of the appended claims.

What is claimed is:

1. A tablet for the sustained release of metoprolol or a salt thereof, comprising:

metoprolol or a pharmaceutically acceptable salt thereof in an amount necessary to render a therapeutic effect in a human patient;

a sustained release excipient comprising a heteropolysaccharide gum and a homopolysaccharide gum capable of crosslinking said heteropolysaccharide gum when exposed to an environmental fluid; an inert pharmaceutical diluent selected from the group consisting of monosaccharide, a disaccharide, a polyhydric alcohol, and mixtures thereof; and a pharmaceutically acceptable cationic cross-linking agent selected from the group consisting of alkali metal and alkaline earth metal sulfates, chlorides, borates, bromides, citrates, acetates, lactates and mixtures thereof, and capable of crosslinking with said gums and increasing the gel strength of said gums when the dosage form is exposed to an environmental fluid; the ratio of metoprolol to said gums being from about 1:1 to about 1:5, said dosage form providing a sustained release of metoprolol for at least about 24 hours when exposed to an environmental fluid.

2. The oral solid dosage form of claim 1, wherein said heteropolysaccharide gum comprises xanthan gum and said homopolysaccharide gum comprises locust bean gum in a ratio from about 1:3 to about 3:1.

3. The oral solid dosage form of claim 1, wherein said cationic cross-linking agent comprises from about 1 to about 20 percent of said formulation, by weight.

4. The oral solid dosage form of claim 1, wherein the drug to gum ratio is from about 1:1.5 to about 1:4.

5. The oral solid dosage form of claim 1, wherein said cationic cross-linking agent comprises calcium sulfate.

6. The oral solid dosage form of claim 1, wherein said cationic cross-linking agent comprises about 10 percent of said formulation, by weight.

7. The oral solid dosage form of claim 1, further comprising a hydrophobic polymer selected from the group consisting of an alkylcellulose, an copolymer of acrylic and methacrylic esters, and mixtures thereof, prior to incorporation of said medicament, said hydrophobic polymer being included in said dosage form in an amount effective to slow the hydration of said gums when exposed to an environmental fluid.

8. The oral solid dosage form of claim 7, wherein said hydrophobic polymer comprises ethylcellulose.

9. The oral solid dosage form of claim 7, wherein said hydrophobic material comprises from about 1 to 20 percent of said dosage form, by weight.

10. The oral solid dosage form of claim 7, wherein said hydrophobic polymer comprises from about 5 to about 10 percent of said dosage form, by weight.

11. The oral solid dosage form of claim 1 which is a tablet.

12. The oral solid dosage form of claim 1, which comprises 50 mg, 100 mg, or 200 mg of metoprolol.

13. A method of preparing a 24 hour formulation of metoprolol, comprising:

preparing a sustained release excipient comprising a heteropolysaccharide gum; a homopolysaccharide gum capable of cross-linking said heteropolysaccharide gum when exposed to an environmental fluid; a cationic crosslinking agent selected from the group consisting of alkali metal and alkaline earth metal sulfates, chlorides, borates, bromides, nitrates, acetates, lactate and mixtures thereof and capable of crosslinking with said gums agent to increase the gel strength when said gums are exposed to an environmental fluid, and an inert pharmaceutical diluent;

combining said sustained release excipient with metoprolol or a pharmaceutically acceptable salt to provide a drug:gum ratio from about 1::1 to about 1:5; and tableting the resultant mixture such that each tablet includes a dose of metoprolol sufficient to provide a therapeutic effect for at least about 24 hours.

14. The method of 13, further comprising wet granulating said heteropolysaccharide gum, said homopolysaccharide gum, said cationic cross-linking agent, and said inert diluent prior to incorporating said metoprolol.

15. The method of 13, further comprising adding a hydrophobic material to said mixture of said sustained release excipient and said metoprolol prior to tabletting in an amount effective to slow the hydration of said gums when exposed to an environmental fluid.

16. The method of 15, further comprising wet granulating said mixture of sustained release excipient, said metoprolol, and said hydrophobic material prior to tableting.

17. The method of claim 13, wherein said heteropolysaccharide is xanthan gum, said homopolysaccharide gum is locust bean gum, and the ratio of said xanthan gum to said locust bean gum is from about 1:3 to about 3:1.

18. The method of claim 13, further comprising providing said cationic cross-linking agent in an amount from about 1 to about 20 percent of the tableted formulation, by weight.

19. The method of claim 13, further comprising providing said tableted formulation with a drug to gum ratio from about 1:1.5 to about 1:4.

20. The method of claim 13, wherein said hydrophobic polymer is selected from the group consisting of an alkylcellulose, an copolymer of acrylic and methacrylic esters, and mixtures thereof.

21. The method of claim 15, wherein said hydrophobic polymer comprises ethylcellulose and said cationic cross-linking agent comprises calcium sulfate.

22. The method of claim 15, wherein said hydrophobic material comprises from about 1 to 10 percent of said dosage form, by weight.

23. The method of claim 13, further comprising tableting said mixture of sustained release excipient and metoprolol such that each tablet contains from about 50 mg to about 200 mg metoprolol or a pharmaceutically acceptable salt thereof.

24. A method of treating a patient with metoprolol comprising, preparing a sustained release excipient comprising a heteropolysaccharide gum; a homopolysaccharide gum capable of cross-linking said heteropolysaccharide gum when exposed to an environmental fluid; a cationic crosslinking agent selected from the group consisting of alkali metal alkaline earth metal sulfates, chlorides, borates, bromides, citrates, acetates, lactates and mixtures thereof; and capable of crosslinking with said gums agent to increase the gel strength when said gums are exposed to an environmental fluid, and an inert pharmaceutical diluent;

combining said sustained release excipient with metoprolol or a pharmaceutically acceptable salt to provide a drug:gum ratio from about 1:1 to about 1:5;

tableting the resultant mixture such that a each tablet includes a dose of metoprolol sufficient to provide a therapeutic effect for about 24 hours or more, and administering said tablets to a patient.

25. A tablet for the sustained release of metoprolol or a salt thereof, comprising:

metoprolol or a pharmaceutically acceptable salt thereof in an amount necessary to render a therapeutic effect in a human patient for about 24 hours;

from about 30% to about 60% gum matrix comprising a xanthan gum and locust bean gum in a ratio from about 1:3 to about 3:1;

from about 1 to about 20% by weight of a pharmaceutically acceptable cationic cross-linking agent selected from the group consisting of alkali metal and alkaline earth metal sulfates, chlorides, borates, bromides, citrates, acetates, lactate and mixtures thereof and capable of crosslinking with said gums and increasing the gel strength of said gums when the dosage form is exposed to an environmental fluid; and an inert pharmaceutical diluent selected from the group consisting of monosaccharide, a disaccharide, a polyhydric alcohol, and mixtures thereof.

26. The oral solid dosage form of claim 25 which is a tablet.

27. The oral solid dosage form of claim 26, wherein the gum matrix comprises from about 35% to about 50% of said dosage form, by weight.

28. The oral solid dosage form of claim 26, wherein the ratio of metoprolol to said gums is from about 1:1 to about 1:5.

29. The oral solid dosage form of claim 26, wherein the drug to gum ratio is from about 1:1.5 to about 1:4.

30. The oral solid dosage form of claim 26, wherein said cationic cross-linking agent comprises calcium sulfate.

31. The oral solid dosage form of claim 26, wherein said cationic crosslinking agent comprises about 10 percent of said formulation, by weight.

32. The oral solid dosage form of claim 26, further comprising from about 1 to 20 percent of a hydrophobic polymer selected from the group consisting of an alkylcellulose, an copolymer of acrylic and methacrylic esters, and mixtures thereof.

33. The oral solid dosage form of claim 32, wherein said cationic cross-linking agent comprises calcium sulfate and said hydrophobic polymer comprises ethylcellulose.

34. The oral solid dosage form of claim 26, which comprises 50 mg, 100 mg, or 200 mg of metoprolol.

* * * * *